US00PP22660P2

(12) United States Plant Patent
Smith

(10) Patent No.: US PP22,660 P2
(45) Date of Patent: Apr. 17, 2012

(54) ***CHRYSANTHEMUM* PLANT NAMED 'SYNWIL YEL'**

(50) Latin Name: *Chrysanthemum×morifolium*
Varietal Denomination: Synwil Yel

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 36 days.

(21) Appl. No.: 12/925,583

(22) Filed: Oct. 25, 2010

(51) Int. Cl.
*A01H 5/00* (2006.01)

(52) U.S. Cl. ..... Plt./289

(58) Field of Classification Search ..... Plt./289
See application file for complete search history.

*Primary Examiner* — June Hwu
(74) *Attorney, Agent, or Firm* — S. Matthew Edwards

(57) ABSTRACT

A new *Chrysanthemum* plant named 'Synwil Yel' particularly distinguished by the medium to large inflorescences with yellow colored ray florets, dark yellow-green foliage, good compact mounded habit, and a natural flowering season in later September.

1 Drawing Sheet

Latin name of the genus and species of the plant claimed: *Chrysanthemum×morifolium.*

Varietal denomination: 'Synwil Yel'.

BACKGROUND OF THE NEW PLANT

The present invention comprises a new *Chrysanthemum*, botanically known as *Chrysanthemum×morifolium*, and hereinafter referred to by the variety name 'Synwil Yel'.

'Synwil Yel' is a product of a planned breeding program. The new cultivar has medium to large inflorescences with yellow colored ray florets, dark yellow-green foliage, good compact mounded habit, and a natural flowering season in later September.

'Synwil Yel' originates as a natural whole plant mutation of 'Yowilma', U.S. Plant Pat. No. 18,924. 'Synwil Yel' was discovered outdoor in a large quantity trial format and selected by the inventor as a single flowering plant within a population of the parent cultivar in a controlled breeding program in Alva, Fla. in November 2006. The parent cultivar 'Yowilma' has white flower color and is somewhat of a faster flowering response in both shaded and natural season crops.

The first act of asexual reproduction of 'Synwil Yel' was accomplished when vegetative cuttings were propagated from the initial selection in December 2006 in a controlled environment in Alva, Fla.

BRIEF SUMMARY OF INVENTION

Horticultural examination of plants grown from cuttings of the plant initiated in December 2006, and continuing thereafter, has demonstrated that the combination of characteristics as herein disclosed for 'Synwil Yel' are firmly fixed and are retained through successive generations of asexual reproduction.

'Synwil Yel' has not been observed under all possible environmental conditions. The phenotype may vary significantly with variations in environment such as temperature, light intensity and day length.

A Plant Breeder's Right for this cultivar was applied for in Canada on Oct. 30, 2009 (09-6772). 'Synwil Yel' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Synwil Yel' with colors being as true as possible with an illustration of this type. The photographic drawing shows a flowering potted plant of the new variety, and a close-up of the flowers.

DETAILED BOTANICAL DESCRIPTION

The plant descriptions and measurements were taken in Gilroy, Calif. in August 2009 under natural light. These plants were about 10 weeks old. The aforementioned photographs were taken in Gilroy, Calif. in late October 2009 outdoors. These plants were approximately 12 weeks of age.

Color references are made to The Royal Horticultural Society Colour Chart (R.H.S.) 2001.

TABLE 1

DIFFERENCES BETWEEN THE NEW VARIETY 'SYNWIL YEL' AND A SIMILAR VARIETY: 'MERMAID YELLOW IMPROVED' (U.S. Plant Pat. No. 18,905)

| | 'Synwil Yel' | 'Mermaid Yellow Improved' (U.S. Plant Pat. No. 18,905) |
|---|---|---|
| Ray floret color: | RHS 3A | RHS 8A |
| Inflorescence diameter: | Smaller | Larger |
| Natural season flowering response: | 1 week faster | 1 week slower |

Plant:

*Form, growth and habit.*—Herbaceous decorative garden-type; stems upright and outwardly spreading, freely branching, strong and moderately vigorous growth habit.

*Plant height.*—20-22 cm.
*Plant height (inflorescence included).*—22-24 cm.
*Plant width.*—34-37 cm.
*Garden performance and tolerance to weather.*—Very good.

Roots:
*Number of days to initiate roots.*—4 days at about 22 degrees C.
*Number of days to produce a rooted cutting.*—10-12 days at 22 degrees C.
*Type.*—Fine, fibrous, free branching.
*Color.*—RHS N155B but whiter.

Foliage:
*Arrangement.*—Alternate, simple.
*Immature, leaf color, upper surface.*—RHS 147A.
*Lower surface.*—Closest to RHS 137A.
*Mature, leaf color, upper surface.*—RHS 147A.
*Lower surface.*—Closest to RHS 137A.
*Length.*—3.2-4.0 cm.
*Width.*—2.8-3.2 cm.
*Shape.*—Ovate.
*Base shape.*—Attenuate.
*Apex shape.*—Mucronulate.
*Margin.*—Palmately; irregularly lobed; irregularly serrate.
*Texture, upper surface.*—Bifid T-shaped hairs.
*Lower surface.*—Heavily Bifid T-shaped hairs.
*Color of veins, upper surface.*—Closest to RHS 147A.
*Color of veins, lower surface.*—RHS 137B.
*Petiole color.*—Closest to RHS 147A.
*Length.*—0.9-1.2 cm.
*Diameter.*—0.2 cm.
*Texture.*—Heavily Bifid T-shaped hairs.

Stem:
*Quantity of main branches per plant.*—About 20.
*Color of stem.*—Closest to RHS 147B but a little greener.
*Length of stem.*—19-22 cm.
*Diameter.*—0.3 cm.
*Length of internodes.*—1.5-3.5 cm.
*Texture.*—Heavily Bifid T-shaped hairs.
*Color of peduncle.*—Closest to RHS 147B.
*Length of peduncle.*—5.0-6.0 cm.
*Peduncle diameter.*—0.25-0.3 cm.
*Texture.*—Heavily Bifid T-shaped hairs.

Inflorescence:
*Type.*—Compositate type, solitary inflorescences (decorative-type) borne terminally above foliage, ray florets arranged acropetally on a capitulum.
*Natural season flowering.*—Late September.
*Quantity of inflorescences per plant.*—About 60 open flowers and 100-125 buds.
*Lastingness of individual blooms on the plant.*—About 4 weeks.
*Fragrance.*—Slightly spicy.

Bud (just when opening/showing color):
*Color.*—RHS 4C.
*Length.*—1.0-1.5 cm.
*Width.*—1.0 cm.
*Shape.*—Oblate.

Immature inflorescence:
*Diameter.*—3.0-3.6 cm.
*Color of ray florets, upper surface.*—RHS 2A but brighter.
*Lower surface.*—Between RHS 3C and RHS 3D.

Mature inflorescence:
*Diameter.*—4.8-5.2 cm.
*Depth.*—2.0-2.5 cm.
*Total diameter of 'disc'.*—No disc showing.
*Recepticle height.*—0.4-0.5 cm.
*Recepticle diameter.*—0.4-0.5 cm.

Ray florets:
*Average quantity of florets.*—175 in numerous whorls.
*Color of florets, upper surface.*—RHS 3A.
*Lower surface.*—RHS 3C.
*Length.*—2.1-2.9 cm.
*Width.*—0.55-0.7 cm.
*Shape.*—Oblong.
*Apex shape.*—Obtuse to slightly retuse or even emarginate.
*Margin.*—Entire.
*Texture, upper surface.*—Papillose.
*Lower surface.*—Papillose.

Disc florets:
*Average quantity of florets.*—Sometimes 1.
*Color of florets.*—RHS 147D.
*Length.*—0.1 cm.
*Width.*—0.2 cm.
*Shape.*—Tubular, elongated.
*Apex shape.*—Acute, 5 pointed.

Phyllaries:
*Quantity.*—20-25.
*Color, upper surface.*—Closest to RHA 137A.
*Lower surface.*—Closest to RHS 147A but appears more grey due to hairs.
*Length.*—0.4-0.6 cm.
*Width.*—0.15-0.2 cm.
*Shape.*—Lanceolate.
*Apex shape.*—Acute.
*Based.*—Fused.
*Margins.*—Entire; papery.
*Texture, upper surface.*—Smooth and glossy.
*Lower surface.*—Heavily bifid T-shaped hairs.

Reproductive organs:
*Pistil.*—1.
*Found on both florets.*—Yes.
*Length.*—0.4-0.5 cm.
*Style color.*—RHS 1B.
*Style length.*—0.4 cm.
*Stigma color.*—RHS 1B.
*Stigma shape.*—Bi-parted.
*Ovary color.*—RHS 155C.
*Stamens.*—1.
*Found on disc florets only.*—Yes.
*Color of filaments.*—RHS 1C.
*Length filaments.*—2.0 cm.
*Anther color.*—RHS 6C.
*Anther length.*—0.15 cm.
*Anther shape.*—Oblong.
*Color of pollen.*—RHS 7A.
*Pollen amount.*—Moderate.
*Fertility/seed set.*—Has not been observed on this hybrid.

Disease/pest resistance: Disease/pest resistance has not been observed on this hybrid.

What is claimed is:

1. A new and distinct variety of *Chrysanthemum* plant named 'Synwil Yel' substantially as illustrated and described herein.

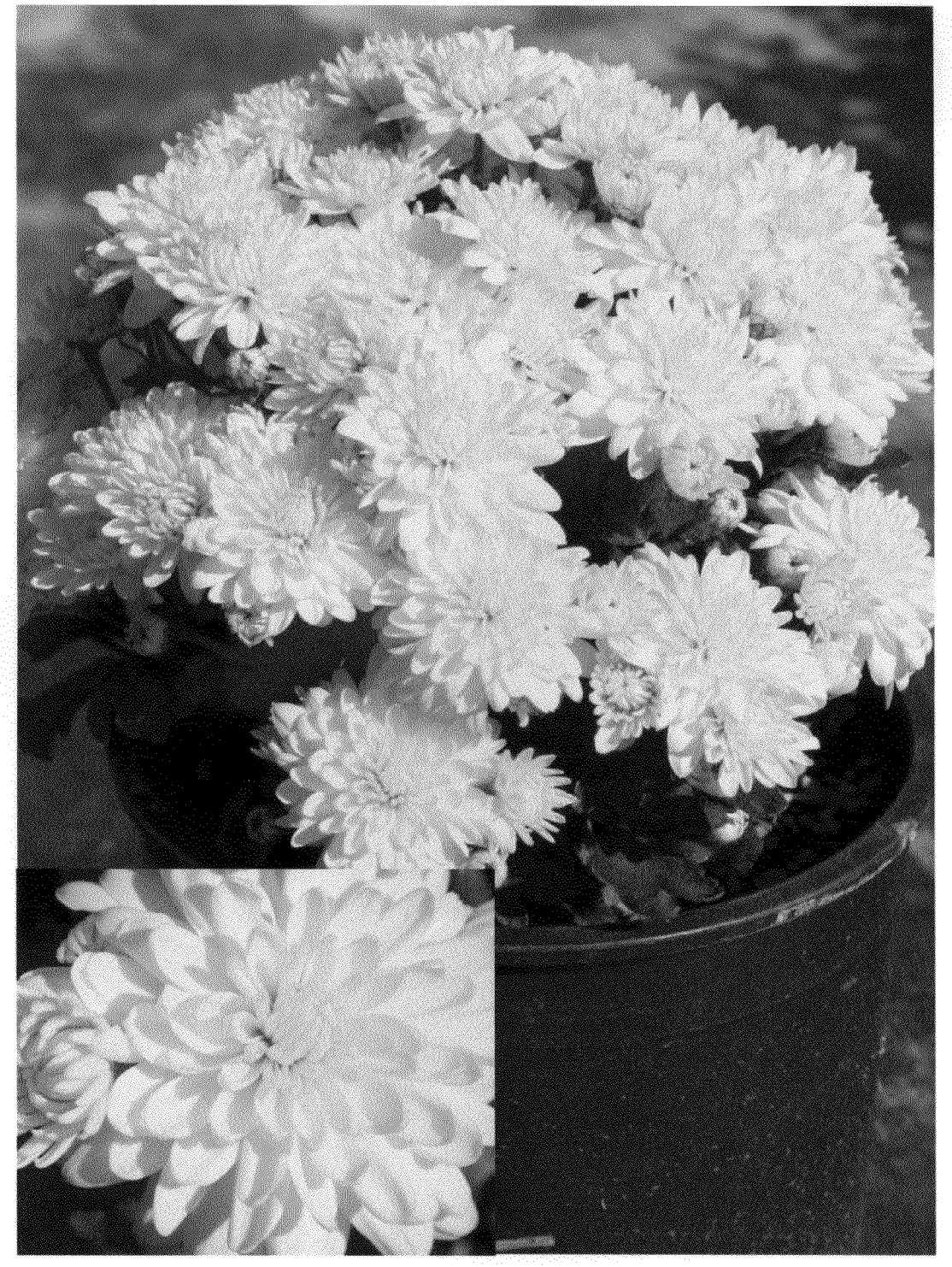

* * * * *